United States Patent [19]

Moore

[11] Patent Number: 4,563,897

[45] Date of Patent: Jan. 14, 1986

[54] APPARATUS FOR MONITORING TOOL LIFE

[75] Inventor: Arthur I. W. Moore, Melton Mowbray, England

[73] Assignee: Production Engineering Research Assoc., Melton Mowbray, England

[21] Appl. No.: 570,180

[22] Filed: Jan. 12, 1984

[30] Foreign Application Priority Data

Jan. 12, 1983 [GB] United Kingdom ............... 8300792

[51] Int. Cl.[4] ............................................. G01N 29/04
[52] U.S. Cl. ........................................ 73/587; 73/104; 364/475
[58] Field of Search .................... 73/104, 587, 593; 364/475, 551, 580

[56] References Cited

U.S. PATENT DOCUMENTS

| | | | |
|---|---|---|---|
| 3,872,285 | 3/1975 | Shum et al. | 73/104 |
| 4,220,995 | 9/1980 | Shoda | 73/104 |
| 4,471,444 | 9/1984 | Yee et al. | 73/104 |

Primary Examiner—Anthony V. Ciarlante
Attorney, Agent, or Firm—Robert H. Ware; Melvin I. Stoltz; Alfred A. Fressola

[57] ABSTRACT

A system for monitoring the vibration of a power driven cutting tool during machining first produces a signal proportional to the vibration spectrum of the tool over a preselected band width. This is passed through a digitally controlled attenuator which is adjusted to provide an output signal at a preselected level. The degree of attenuation is stored, as is a reference value which is generated as a function of the attenuated signal. Then, during subsequent machining operations under the same machining conditions the attenuator is controlled to provide the same degree of attenuation and the reference value, which is in the form of a digital signal, is compared with the rectified and digitized output of the attenuator. When the latter exceeds the reference value a control signal is generated which either provides an audible or visual warning that the cutting tool is worn and therefore due for replacement or initiates an automatic tool changing operation. The system effectively monitors the wear of the tool and, in providing its own reference, i.e. the reference value which is generated, caters automatically for changes in the machining conditions such as use of a different tool or change in workpiece material.

40 Claims, 4 Drawing Figures

APPARATUS FOR MONITORING TOOL LIFE

The present invention relates to apparatus for monitoring the operating condition of cutting tools such as are used in machine tools, such as lathes, drilling machines and machining centres.

It is generally impossible to predict accurately the useful life of a cutting tool such as a high speed steel twist drill which is used under a given set of operating conditions, e.g. cutting speed and feed rate, but it is of course essential to ensure that a tool is withdrawn from use before total failure becomes a distinct possibility. An undetected broken tool in, for example an automatic lathe, can cause catastrophic damage to the workpiece, tooling and also to the machine itself. In a typical example an automated machine might attempt to tap a thread in a hole which is not present because a twist drill normally used to drill such holes has broken.

Naturally, great reliance is placed upon a machine operator to monitor the condition of a tool in use and decide when it should be replaced. A consequence of this is that tools often tend to be discarded well before the end of their useful life resulting in unnecessarily long machining times and poor tool utilisation.

In automated and semi-automated machines there is an even greater tendency to "under-run" tools because of the even more severe consequences of undetected tool failure.

In a prior system developed by the applicants for monitoring the operating condition of a cutting tool a preselected frequency band of vibration of the tool is monitored through a vibration sensor and a bandpass filter and the resulting vibration signal is converted to a d.c. voltage which varies with the amplitude of the frequency of vibration. The d.c. voltage is compared with two different preset trip levels to (i) generate a warning signal and (ii) disengage the tool from the workpiece respectively when the levels are reached. This system is primarily applicable to machining situations where a number of workpieces of the same type are machined successively by a single tool of a given type at preselected machining conditions i.e. speed, feed rate, depth of cut etc., and the trip levels are chosen manually by reference to previous experimental results obtained by testing a tool of the relevant type on one particular workpiece under the same machining conditions.

However, since the acceptable amount of wear on a tool depends on the machining conditions (a tool for machining e.g. bronze, utilizes cutting conditions different from those for machining e.g. steel) the reference vibration level with which the vibration spectrum of the tool is compared will differ for different machining conditions. In general because soft materials are machined at higher cutting speeds than hard materials, the vibration level for soft materials is higher than that for hard materials. Therefore, using a reference vibration level obtained from a tool machining a hard material may result in a tool which is monitored while machining a softer material being discarded too early while, conversely, a tool which is monitored while machining a harder material may fail in use before a reference vibration level is reached, and will not be detected.

The present invention seeks to provide an improved system for monitoring the operating condition of a cutting tool.

Accordingly, the present invention provides a method of monitoring the operating condition of a cutting tool during machining of a workpiece comprising the steps of (a) monitoring the level of vibration of the tool on commencement of machining and generating a first signal representative of said monitored level, (b) applying said first signal to a variable gain circuit means to provide a second signal which is a function of said first signal, (c) adjusting the gain of said gain circuit means to adjust said second signal to a preselected value, (d) generating at least one reference value which is a preselected function of said preselected value, (e) storing said reference value and a factor representing the adjusted gain of said gain circuit means, (f) prior to commencing subsequent machining under the same or similar machining conditions, adjusting the gain of said gain circuit to said adjusted gain, and on commencement of said subsequent machining (g) monitoring the level of vibration of the tool to generate a further second signal, (h) comparing said further second signal with said reference value and generating a control signal independence on said further second signal level exceeding said reference value.

The present invention also provides a system for monitoring the operating condition of a cutting tool during machining of a workpiece comprising monitoring means for monitoring the level of vibration of the tool on commencement of machining and generating a first signal representative of said monitored level;

a variable gain circuit means for providing a second signal which is a function of said first signal;

control means for automatically adjusting the gain of said gain circuit means to adjust said second signal to a preselected value;

reference means for generating at least one reference value which is a preselected function of said preselected value;

store means for storing said reference value and a factor representing the adjusted gain of said gain circuit means;

comparator means for comparing further second signals, generated during subsequent machining under the same or similar machining condictions, with said reference value and generating a control signal in dependence on said further second signal level exceeding said reference value.

The term "vibration" as used herein means any mechanical wave displacement, velocity or acceleration emitted by a tool when in use and encompasses the phenomenon known as "acoustic emission".

The term "machining conditions" as used herein refers to controlled factors in which, in a machining operation using a cutting tool, changes could give rise to substantial alterations in the tool vibration during machining, and specifically including: cutting tool type, cutting speed, feed rate, depth of cut and workpiece material. A change in one of these factors would result in a change in machining conditions.

The main advantage of the present invention is that a "signature" of a particular machining condition is automatically produced against which actual tool vibration can be compared to indicate the state of wear of the tool.

The present invention is further described hereinafter, by way of example, with reference to the accompanying drawings, in which.

Figure 1:
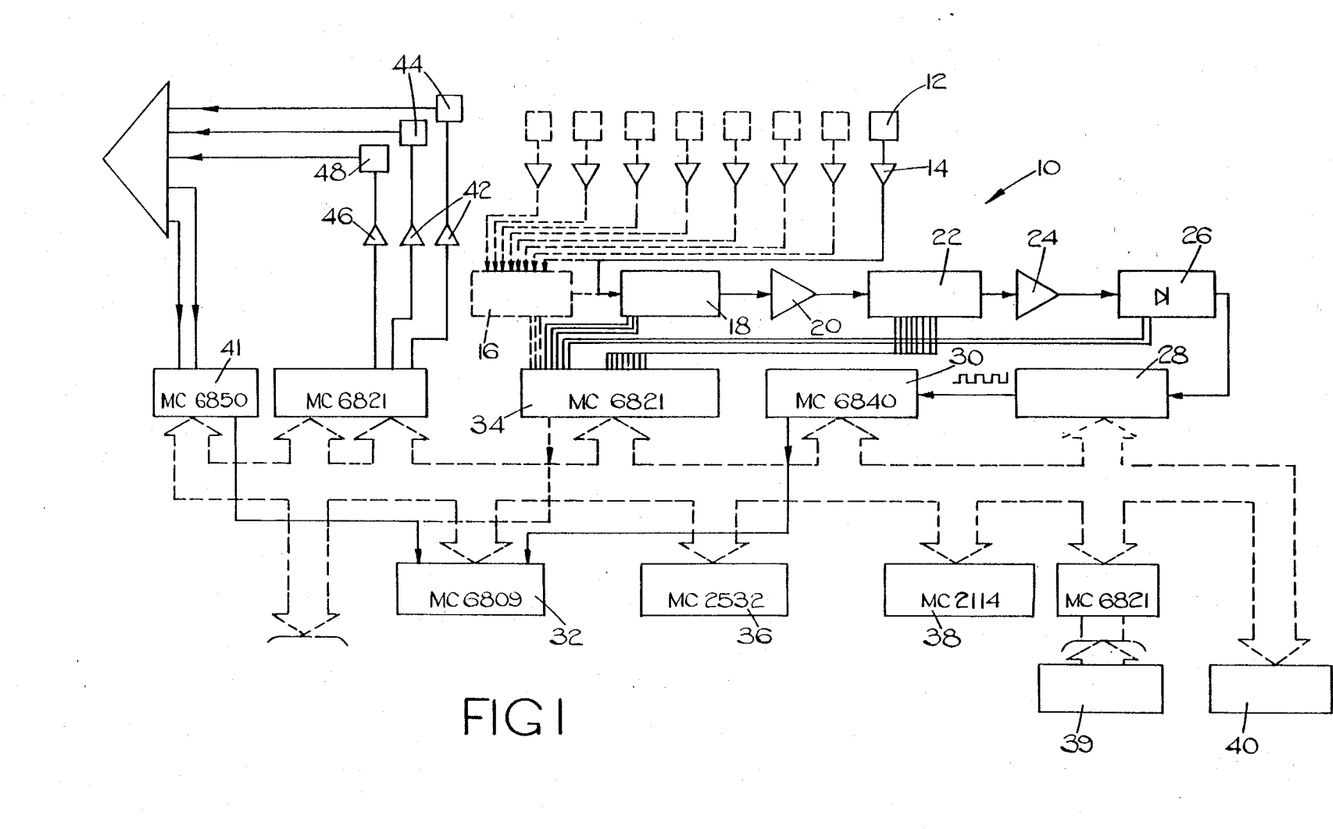
FIG. 1 is a schematic circuit diagram of a system according to the present invention.
Figure 2:
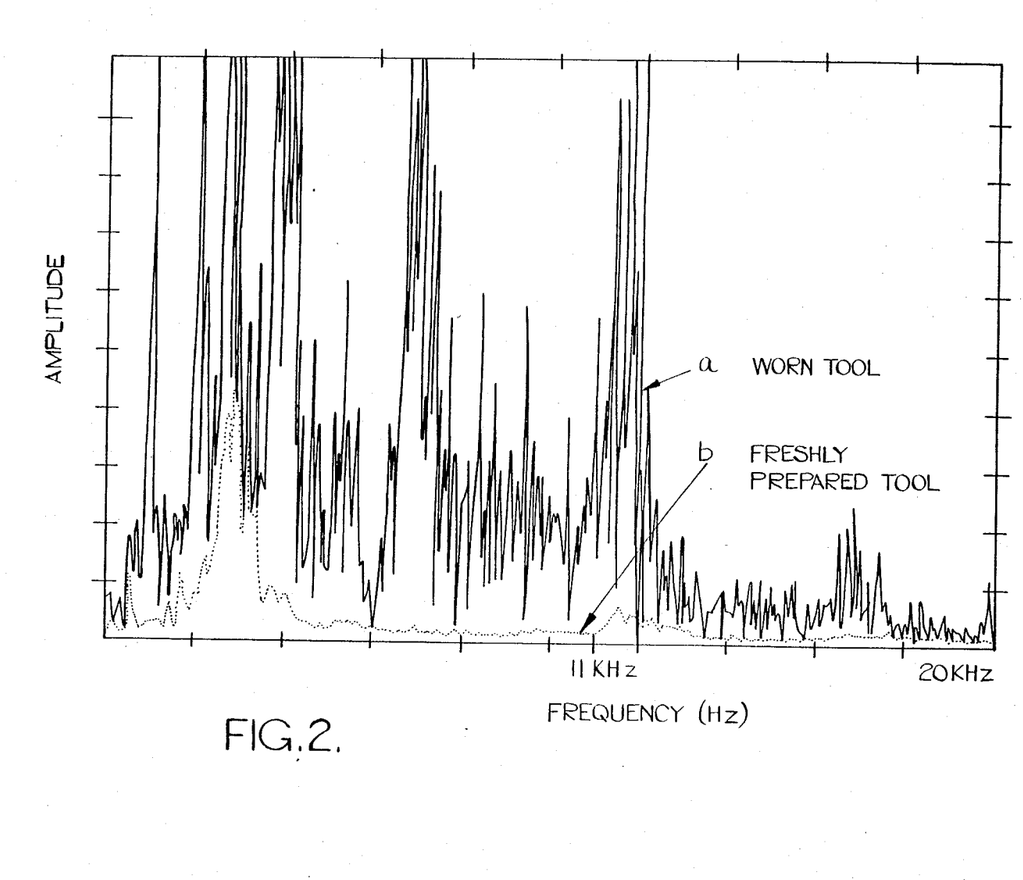
FIG. 2 is a graph showing the variation in amplitude of vibration against frequency for both a worn cutting tool and a freshly-prepared cutting tool when used in a machine tool.

The circuit 10 shown in FIG. 1 is designed to monitor the vibration produced by tool and workpiece interaction in a machine tool such as a numerical control machine tool in a series of machining situations in which a multiplicity of different machining conditions operate sequentially. The different machining conditions may result from the use of different tool types in the machine, changes in tool cutting speed and the like during machining of batch workpieces. The circuit 10 has a vibration sensor in the form of, e.g., an accelerometer 12 which is arranged so that as the tool operates on a workpiece the predominant vibrations produced are detected by the accelerometer. The latter generates an electrical signal which is representative of the vibration generated at the tool-workpiece interface and this signal is transmitted through a buffer amplifier 14 to an attenuator 18, impedance-matching buffer amplifier 20, a bandpass filter 22, preferably a variable, binary switched filter, and highgain amplifier 24 to a full wave rectifier 26. The analogue output of the rectifier 26 is connected to a voltage-to-frequency converter 28 which gives a digital output fed to a programmable timer 30 in turn connected to a microprocessor 32. The microprocessor 32 is also coupled through a parallel interface circuit 34 to control digitally the attenuator 18, filter 22 and rectifier 26. The microprocessor 32 is also coupled through a system bus line to the timer 30, voltage-to-frequency converter 28 and a programmable memory (ROM) 36, a programmable workspace (RAM) 38, a data entry keypad 39 and display terminal 40, and a serial interface 41 which inputs information to the microprocessor 22 received from the machine tool controller such as a code signal identifying each machining condition.

In normal operation, the system is manually programmed by means of the data entry terminal 39 before operation, data relating to machining conditions, such as cutting tool type to be monitored, the monitored frequency band and maximum permissible level of vibration being entered by means of a simple programme or automatically by a computerised control system which is independent of the data entry terminal and by means of which the machine tool is controlled. Different values of the frequency band and/or the level of vibration may be selected for different machining conditions so that for example, different values may be programmed for each tool type. In operation, during machining the vibration level at each cutting tool—workpiece interface at the monitored frequency relevant to that tool is compared to the permissible programmed level, the vibration level preferably being sampled over an 80 ms period at about 80 ms intervals. When the monitored vibration level exceeds the programmed level a trip is activated to signal a tool change requirement, stop the operation of the machine tool and/or disengage the tool and workpiece. The system of FIG. 1 has two trips which are triggered through respective driver amplifiers 42 and relays 44 and are actuated at different levels. The two levels may be set independently of each other but preferably one of the trips is used to warn that the tool is coming to the end of its useful life while the second trip is activated to stop the operation of the tool or signal a tool change requirement with the ratio of the two trip levels being preselectable so that the setting of the second trip level automatically sets the first trip level. The first trip level is preferably adjustable as a percentage of the second trip level in the range of 0–100%. At 100% the two trip leads become one.

A further trip is also provided and is actuated through a relay driver 46 and relay 48 to stop operation of the machine tool if a certain minimum level of tool vibration has not been reached within a programmed time interval. This ensures that machining does not commence in the absence of a tool. The programmed time interval can conveniently be varied between 0 and 99.9 seconds in steps of 0.1 seconds although a continuous time variation may also be provided.

The narrow frequency band of the tool frequency vibration spectrum which is monitored is selected using the binary switched filter 22 which can be varied over a preferred frequency range 1.5 KHz to 25 KHz. Advantageously the width of the band monitored may also be varied.

Although the trip levels for the system can be set manually, having been derived from a vibration frequency spectrum obtained from a previously used tool and used as a standard, the present system can be programmed to derive its own trip levels from the vibration frequency spectrum of the tool being monitored. This has the advantage that each machining operation being monitored has its own trip levels automatically set and unique to that operation.

Figure 4:
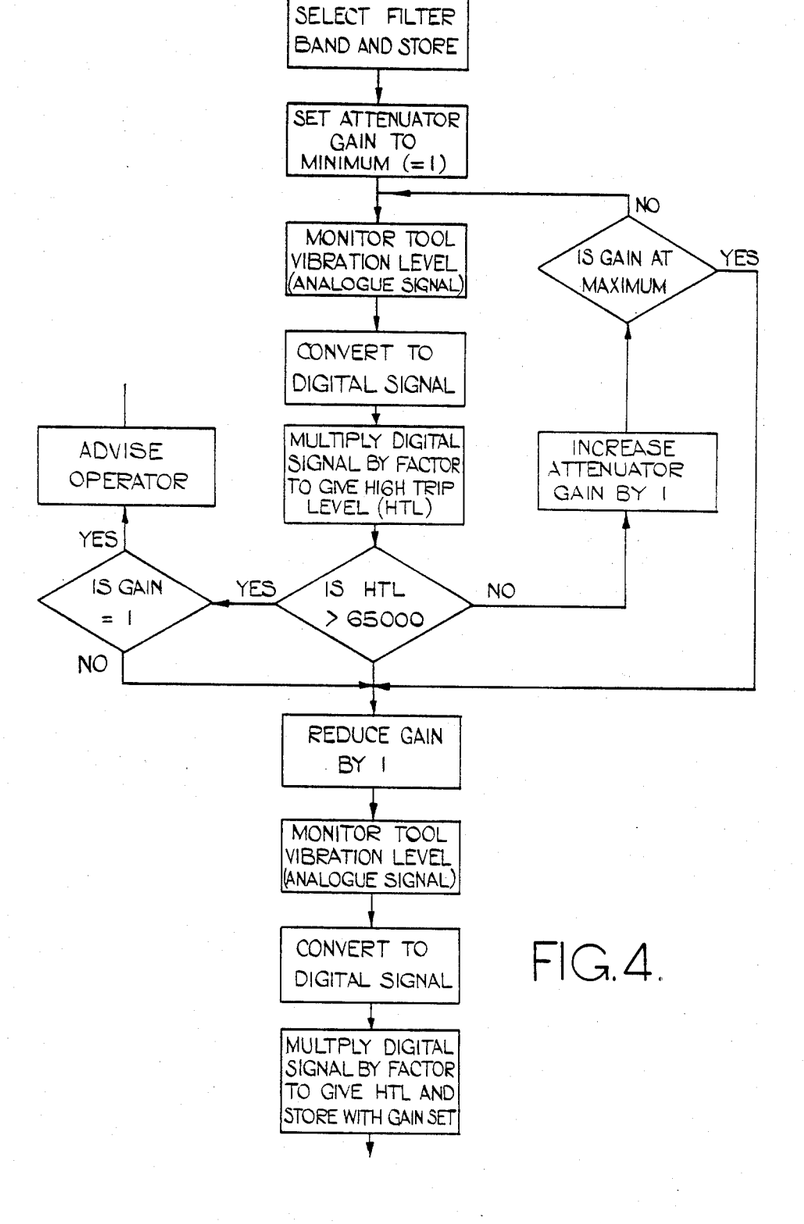
FIG. 4 is a flow chart illustrating the manner in which a "signature" for a particular machining condition is produced.

The procedure for automatically generating the necessary "signature" for a particular machining condition is shown in the flow chart in FIG. 4.

Before machining of a particular workpiece commences using a selected tool in preselected machining conditions the microprocessor 32 selects the required frequency band on the filter 22 and sets the attenuator gain to a selected level, preferably its minimum (i.e. maximum attenuation). This information can be operator selected or received through the serial interface 41 from the control system program of the machine tool. A code identifying the "signature" to be generated is also generated by the microprocessor or manually entered, if necessary, this being used during operation to relate the "signature" to the relevant machining conditions. Once machining commences the vibration level monitored by the system is converted to a digital signal by the converter 28.

Figure 3:
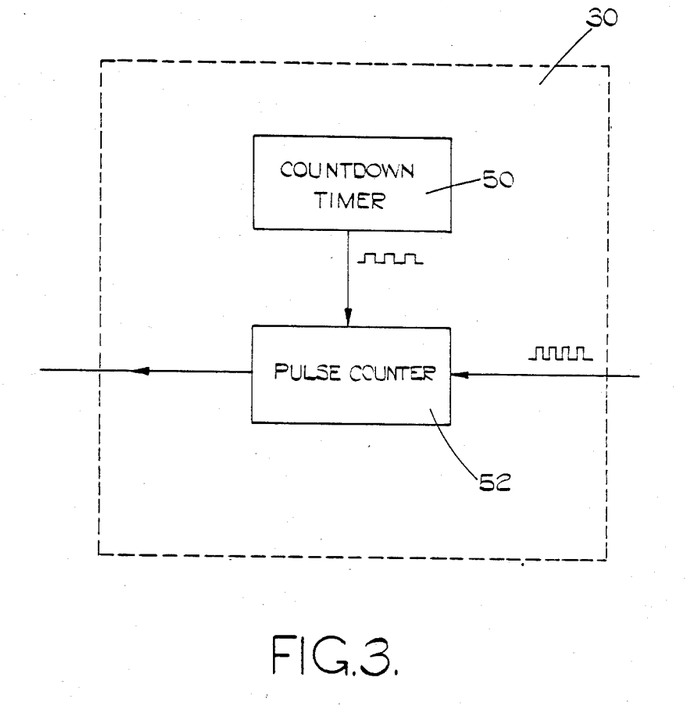
FIG. 3 is an expanded diagram of the programmable timer of FIG. 1.

This digital signal, which is a square wave signal whose frequency is proportioned to the monitored vibration amplitude, is sampled by the timer 30 which is shown in detail in FIG. 3 and comprises a countdown timer 50 and pulse counter 52. The output of the converter 28 is fed to the pulse counter 52 which is "gated" by gate pulses from the countdown timer 50. Each gate pulse is preferably 80 ms duration at an interval of 80 ms to provide 12 pulses/second. The pulse counter 52 counts the number of input pulses over the 80 ms period and this count is then multiplied by the microprocessor 32 by a preset factor to give a High Trip level (HTL).

The factor has previously been input either by an operator or by the machine tool control system programme.

The HTL number is then compared by the microprocessor 32 with a preset number, in this instance 65000. If the HTL is less than 65000 then the attenuator gain is increased by 1 and the process repeated to give a new HTL. If HTL is greater than 65000 or the attenuator gain is maximum then, provided the gain is not 1, the gain is reduced by 1, the new HTL calculated for this new gain and stored in the system memory together with the attenuator gain and selected filter band to provide a machining "signature". If desired, a second, lower trip level (LTL) is also generated as a preselected function of HTL and stored. This can be used to warn that a tool is approaching the end of its useful life. A machining "signature" is then available for use in all machining operations in which the same machining conditions apply so that when a machining operation is commenced in which the same or similar machining conditions apply the filter 22, gain of the attenuator, HTL and LTL are automatically set according to the relevant "signature" which is called from the memory by the microprocessor.

In addition to the above, the vibration level monitored by the system is compared with preselected minimum reference level and, if the monitored level remains lower than the reference level for a preselected time period, indicating that the tool is not cutting when it should be, the machining operation is aborted. If the monitored vibration level reaches the minimum reference level then machining continues until the monitored vibration level reaches the lower trip level which triggers a warning that the tool is approaching the end of its useful life. When the monitored vibration level reaches the higher trip level then the machine operation is automatically stopped and, where appropriate, a tool change operation actuated. The same procedure is applied for each type of machining operation carried out on a workpiece and if the higher trip level is not reached during a machining operation effected on the first workpiece then that machining operation is repeated on the next and successive workpieces using the same tool and "signature". If a tool is replaced by an identical tool for machining the same workpiece type the same stored "signature" is used and the machining operation proceeds as described, although a new "signature" could be generated if desired. The first trip level can also be used to initiate a tool change, if desired.

Where different machining conditions apply for a machine tool such as where more than one tool type is used, the procedure applies equally to each set of machining conditions. Where a tool breaks or suffers damage such as chipping or frittering the vibration will be sufficiently high to exceed the high trip level.

Although the system is described as being designed to monitor via a single sensor 12 the vibration of a number of cutting tools used sequentially, it will be appreciated that the system can be altered to monitor simultaneous machining operations using several parallel sensors. The sensors can be on a single maching tool with multiple spindle heads or on several machine tools each having single or multiple spindle heads. The relevant "signatures", i.e. datum and trip levels are established for the respective machining conditions as is described above with reference to FIG. 1 and then each time a machining condition is repeated the actual vibration level is compared only with the relevant "signature".

In this case where several sensors 12 are used these are coupled through a multiplexer 16 to the attenuator, the sensor outputs being coupled sequentially under the control of the microprocessor 32.

In a modification to the above-described system the maximum tool vibration levels which are monitored are stored and the microprocessor scans the stored values sequentially to compare them with the reference "signature". The advantage of this is that it reduces the time during which the vibration level of any one tool is not being compared with its "signature". This is particularly important in detecting breakage of a tool since an undetected broken tool can do considerable damage in a very short time.

One advantage of a system according to the present invention in which automatic generation of vibration datum and trip levels is effected is that variations in machinability of work materials which may occur from batch to batch is automatically catered for.

The vibration of a cutting tool which is monitored by an apparatus according to the present invention can be any type of mechanical signal produced by the tool during use. Various transducers are available which permit monitoring of displacement, velocity or acceleration. A preferred form is a piezo-electric accelerometer sensor. Another type of sensor uses so-called acoustic emission which is a term applied to the low level stress wave emitted by a solid material when it is deformed or ruptured in association with relief of strain energies.

The detection of acoustic emission is conveniently effected using an acoustic emission sensor attached to the tool shank, toolholder or machine tool spindle head to provide an electrical signal representative of the detected vibration. The signal can then be processed in the normal manner. The advantage of acoustic emission measurement is that it is far more sensitive to the monitoring of the production of cracks, chips and the like in tools.

I claim:

1. A method of monitoring the operating condition of a cutting tool during machining of a workpiece comprising the steps of
    (a) monitoring the level of vibration of the tool on commencement of machining and generating a first signal representative of said monitored level,
    (b) applying said first signal to a variable gain circuit means to provide a second signal which is a function of said first signal,
    (c) adjusting the gain of said gain circuit means to adjust said second signal to a preselected value,
    (d) generating a first reference value which is a preselected function of said preselected value and generating a second reference value representing a minimum reference level generated when the cutting tool commences machining a workpiece,
    (e) storing said first and second reference values and a factor representing the adjusted gain of said gain circuit means,
    (f) prior to commencing subsequent machining under the same or similar machining conditions, adjusting the gain of said gain circuit to said adjusted gain, and on commencement of said subsequent machining
    (g) monitoring the level of vibration of the tool to generate a further second signal,
    (h) comparing said further second signal with said first reference value and generating a first control signal in dependence on said further second signal level exceeding said reference value and generating a second control signal if the monitored level is less than the second reference value for a predetermined length of time;

whereby generation of the first control signal is indicative of a worn or defective cutting tool and generation of the second control signal is indicative of a broken or missing cutting tool.

2. A method as claimed in claim 1 further comprising to step (a), selecting a frequency band of a variable bandpass filter over which cutting tool vibration is to be monitored, subsequently storing a factor representing said selected frequency band, and in step (f) adjusting said filter to said selected frequency band.

3. A method as claimed in claim 2 wherein said filter is a digitally controlled filter and said factor is a digital control signal for said filter.

4. A method as claimed in claim 1, 2 or 3 wherein prior to step (b) or (c) the gain of said gain circuit means is reduced to a preselected value.

5. A method as claimed in claim 4 wherein said preselected value is minimum gain.

6. A method as claimed in claim 5 wherein step (c) comprises:
comparing said second signal with a preselected reference and adjusting the gain of said circuit until said second signal value is said preselected value.

7. A method as claimed in claim 6 wherein step (c) comprises (i) acting on second signal to provide a product signal greater than said second signal and a present function of said second signal, (j) comparing said product signal with a further preselected reference value, (k) if said product signal value is less than said further reference value, increasing the gain of said gain circuit means, (1) repeating steps (i), (j) and (k) until said product signal is greater than said further reference value, (m) reducing the gain of said gain circuit means by a preset factor, and (n) repeating step (i) and storing said product signal as said first reference value.

8. A method as claimed in claim 7 wherein the output of said gain circuit means is converted to a digital signal to provide said second signal.

9. A method as claimed in claim 8 for monitoring the operating condition of a plurality of power driven cutting tools during machining of a respective workpiece under the same or similar machining conditions comprising, carrying out steps (a) to (e) of claim 1 for one of said tools, and subsequently carrying out steps (f) to (h) of claim 1 for each said tool.

10. A method as claimed in claim 8 for monitoring the operating condition of a plurality of power driven cutting tools during machining of a respective workpiece under different machining conditions comprising, carrying out steps (a) to (e) of claim 1 for each said tool and subsequently carrying out steps (f) to (h) of claim 1 for each said tool using the respective stored first and second reference values and adjusted gain associated with said tool.

11. A system as claimed in claim 10 wherein the respective maximum value of said adjusted second signal for each said tool is stored and each said stored maximum value is sequentially compared with the respective reference value to provide the respective control signature.

12. A method as claimed in claim 11 comprising providing a visual or audible warning in response to generation of the first-mentioned control signal and further comprising the step of generating a third reference value less than or greater than said first reference value, comparing said third reference value with said further second signal and generating a third control signal in dependence on said further second signal level exceeding said third reference value.

13. A method as claimed in claim 12 wherein the first-mentioned reference value is a preselectable percentage value of the third reference value.

14. A method as claimed in claim 13 wherein said percentage value lies in the range 0 to 100.

15. A method as claimed in claim 14 comprising initiating a tool change in response to generation of the third control signal.

16. A system for monitoring the operating condition of a cutting tool during machining of a workpiece comprising monitoring means for monitoring the level of vibration of the tool on commencement of machining and generating a first signal representative of said monitored level;

a variable gain circuit means for providing a second signal which is a function of said first signal;

control means for automatically adjusting the gain of said gain circuit means to adjust said second signal to a preselected value;

reference means for generating a first reference value which is a preselected function of said preselected value and for generating a second reference value representing a minimum reference level generated when the cutting tool commences machining a workpiece;

store means for storing said first and second reference values and a factor representing the adjusted gain of said gain circuit means;

first comparator means for real-time comparing further second signals generated during subsequent machining under the same or similar machining conditions with said first reference value and generating a first control signal in dependence on said further second signal level exceeding said first reference value; and second comparator means for generating a second control signal if the monitored level is less than the second reference signal for a predetermined length of time;

whereby generation of the first control signal is indicative of a worn or defective cutting tool and generation of the second control signal is indicative of a broken or missing cutting tool.

17. A system as claimed in claim 16 further comprising a bandpass filter coupled to said monitoring means, said bandpass filter being a variable bandpass filter and said control means being operable to control the bandpass frequency of said filter.

18. A system as claimed in claim 17 wherein said filter is a digitally controlled filter and said factor is a digital control signal for said filter.

19. A system as claimed in claim 16, 17 or 18 wherein said control means is operable to reduce the gain of said gain circuit means to a preset value prior to adjusting said second signal to a preselected value.

20. A system as claimed in claim 19 wherein said control means is operable to compare said second signal with a preselected reference and adjusting the gain of said gain circuit means until said second signal value is said preselected value.

21. A system as claimed in claim 20 wherein said control means is operable to derive from said second signal a product signal greater than said second signal and a preset function of said second signal, to compare said product signal with a further preselected reference value, to increase the gain of said gain circuit means if said product signal value is less than said further reference value, to repeat the operation until said product signal value is greater than said further reference value, to reduce the gain of said gain circuit means by a preset factor and to derive a further said product signal for storing as said first reference value.

22. A system as claimed in claim 21 further comprising means for converting the output of said gain circuit means to a digital signal to provide said second signal.

23. A system as claimed in claim 22 for monitoring the operating condition of a plurality of cutting tools during machining of a respective workpiece under different machining conditions, wherein said control means is operable to provide a respective adjusted second signal and said reference means is operable to provide a respective first reference value for each said machining condition; and wherein during subsequent machining under machining conditions the same as or similar to one of said different machining conditions said control means is operable to adjust the gain of said gain circuit means to the adjusted gain associated with said one machining condition and said first comparator means is operable to compare further second signals thus generated with the associated respective first reference value and generate a first control signal in dependence on said further second signal level exceeding said first reference value.

24. A system as claimed in claim 23 wherein said control means is a microprocessor.

25. A system as claimed in claim 24 wherein said reference means is operable to generate a third reference value less than or greater than the first-mentioned reference value for comparison with said further second signals to produce a third control signal.

26. A system as claimed in claim 25 further comprising means for storing the respective maximum value of said adjusted second signal for each said tool and sequentially comparing each said stored maximum value with the respective first reference value to provide the respective first control signal.

27. A system as defined in claim 16 wherein the monitoring means are mounted on the cutting tool.

28. A method for monitoring the operating codition of at least one power driven cutting tool during machining of a workpiece comprising the steps of
  (a) monitoring the level of vibration of the tool on commencement of machining and generating a first signal representative of said monitored level;
  (b) applying said first signal to a variable gain circuit means to provide a second signal which is a function of said first signal,
  (c) adjusting the gain of said gain circuit means to adjust said second signal to a preselected value,
  (d) generating a first reference value which is a preselected function of said preselected value and generating a second reference value representing a minimum reference level generated when the cutting tool commences machining a workpiece, and on commencement of subsequent machining
  (e) comparing further second signals with said first reference value and generating a first control signal in dependence on said further second signal level exceeding said reference value and generating a second control signal if the monitored level is less than the second reference value for a predetermined length of time;

whereby generation of the first control signal is indicative of a worn or defective cutting tool and generation of the second control signal is indicative of a broken or missing cutting tool.

29. A system for monitoring the operating condition of a power driven cutting tool during machining of a workpiece comprising monitoring means for monitoring the level of vibration of the tool on commencement of machining and generating a first signal representative of said monitored level;
  a variable gain circuit means for providing a second signal which is a function of said first signal;
  control means for automatically adjusting the gain of said gain circuit means to adjust said second signal to a preselected value;
  reference means for generating a first reference value which is a preselected function of said preselected value and for generating a second reference value representing a minimum reference level generated when the cutting tool commences machining a workpiece;
  first comparator means for comparing further second signals generated during subsequent machining with said first reference value and generating a first control signal in dependence on said further second signal level exceeding said reference value; and
  second comparator means for generating a second control signal if the monitored level is less than the second reference signal for a predetermined length of time;
  whereby generation of the first control signal is indicative of a worn or defective cutting tool and generation of the second control signal is indicative of a broken or missing cutting tool.

30. A system for monitoring the operating conditions of a cutting tool during machining of a work piece comprising:
  (a) means for monitoring the level of vibration of the tool on commencement of machining and generating a first signal representative of said monitored level;
  (b) a variable gain circuit means for providing a second signal which is a function of said first signal;
  (c) control and reference means for automatically adjusting the gain of the gain circuit means so as to adjust the second signal to a preselected value wherein said control and reference means includes means for
    (1) deriving from the second signal a product signal greater than the second signal which is also a preset function of the second signal,
    (2) comparing the product signal with a first preselected reference value,
    (3) increasing the gain of the gain circuit means if the product signal value is less than the first reference value,
    (4) repeating subelements (1) through (3) until the product signal value is greater than the first reference value, and
    (5) reducing the gain of the gain circuit means by a preset factor and deriving a further product signal for storing as a second reference value;
  (d) means for storing the second reference value and a factor representing the adjusted gain of the gain circuit means; and (e) comparator means for real-time comparing further second signals generated during subsequent machining under the same or similar machining conditions with the second reference value and generating a control signal dependent on the further second signal level if it exceeds the second reference value.

31. A system as defined in claim 30 further comprising means for converting the output of the gain circuit means to a digital signal so as to provide said second signal.

32. A system as defined in claim 31 further comprising a digital variable bandpass filter coupled to the monitoring means and wherein the control and reference means further comprises means for producing a digital control signal to control the bandpass frequency of the filter.

33. A system as defined in claim 32 wherein the control and reference means is operable to reduce the gain of the gain circuit means to a preset value prior to adjusting the second signal to a preselected value.

34. A system as defined in claim 33 wherein the control means is operable to compare said second signal with a preselected reference and adjusting the gain of said gain circuit means until said second signal value is said preselected value.

35. A system as defined in claim 34 for monitoring the operating condition of a plurality of cutting tools during machining of a respective workpiece under different machining conditions, where the control and reference means is operable to provide a respective adjusted second signal and further provides a respective second reference value for each said machine condition; and wherein during subsequent machining under machining conditions the same as or similar to one of the said different machining conditions the control and reference means is operable to adjust the gain of the gain circuit means to the adjusted gain associated with one of the machining conditions and wherein the comparator means is operable to compare further second signals thus generated with the associated respective second reference value and to generate a control signal dependent on a further second signal level exceeding the second reference value.

36. A system as defined in claim 35 wherein the control portion of the control and reference comprises a microprocessor.

37. A system as defined in claim 36 wherein the reference portion of the control and reference means is operable to generate a third reference value less than or greater than the second reference value for comparison with further second signals so as to produce a second control signal.

38. A system as defined in claim 30 wherein the control and reference means further generates a third reference value representing a minimum reference level generated when the cutting tool commences machining a work piece, and wherein the store means further stores this third reference value and further comprising second comparator means for generating a second control signal if the monitored level is less than the third reference signal for a predetermined length of time.

39. A system as defined in claim 38 further comprising means for terminating the machining operation if a second control signal is generated by the second comparator means.

40. A system as defined in claim 30 wherein the monitoring means are mounted on the cutting tool.

* * * * *